United States Patent [19]

Pinsker

[11] Patent Number: 5,753,712
[45] Date of Patent: May 19, 1998

[54] TREATMENT OF MIGRAINE HEADACHES AND FORMULATIONS

[76] Inventor: Walter Pinsker, 21 Skookwams Ct., West Islip, N.Y. 11795

[21] Appl. No.: 693,158

[22] PCT Filed: Feb. 18, 1994

[86] PCT No.: PCT/US94/01741

§ 371 Date: Oct. 4, 1996

§ 102(e) Date: Oct. 4, 1996

[87] PCT Pub. No.: WO95/22324

PCT Pub. Date: Aug. 24, 1995

[51] Int. Cl.$^6$ .................... A61K 31/52; A61K 31/135
[52] U.S. Cl. ................................ 514/649; 514/816
[58] Field of Search ........................ 514/649, 816

[56] References Cited

U.S. PATENT DOCUMENTS

| | | | |
|---|---|---|---|
| 3,819,706 | 6/1974 | Mehta | 260/570.5 |
| 3,885,046 | 5/1975 | Mehta | 424/330 |
| 3,961,060 | 6/1976 | Fuxe | 424/253 |

OTHER PUBLICATIONS

Chemical Abstracts AN 1992: 440286, Heal et al. 1992.
BIOSIS abstract No. AN 93:284177, Pinsker, Mar. 1993.
Rac et al. Chemical Abstract No. 1994:491854, Slovak Patent CS 277525 B6, Feb. 17, 1993.

*Primary Examiner*—Keith D. MacMillan
*Attorney, Agent, or Firm*—Ernest V. Linek

[57] ABSTRACT

A method of Treatment of treating migraine headaches in humans by the administration of the compound of the formula I

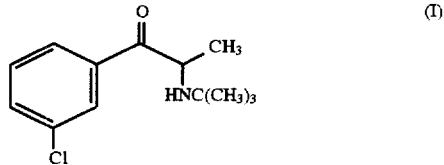

or a pharmaceutically acceptable acid addition salt thereof in a non-toxic, effective therapeutic amount (calculated as base) to a human in need thereof.

3 Claims, No Drawings

TREATMENT OF MIGRAINE HEADACHES AND FORMULATIONS

This application is a 371 of PCT/US94/01741, filed Feb. 18, 1994.

BACKGROUND OF THE INVENTION

This invention is directed to a method of treatment of migraine headaches in humans by the administration to the humans of the compound of the formula I

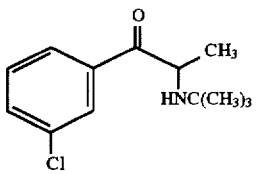

or a pharmaceutically acceptable acid addition salt thereof in a non-toxic, therapeutic amount (calculated as base) to a human in need thereof.

In U.S. Pat. Nos. 3,819,706 and 3,885,046 m-chloro-α-t-butylaminopropiophenone and salts thereof, in particular the hydrochloride salt, were disclosed on being antidepressants. Bupropion hydrochloride is the generic name for m-chloro-α-t-butylaminopropiophenone which is used under the trademark WELLBUTRIN® in the United States of America for the treatment of depressions. The neurochemical mechanism of the antidepressant effect of bupropion is not known.

I have now found that bupropion hydrochloride is effective in treating migraine headaches in humans. It is effective when administered alone or together with caffeine, e.g., with one or two cups of coffee.

The compound of formula (I) (the active ingredient) or the pharmaceutically acceptable acid addition salt thereof is preferably administered in unit dosage form to the human being treated.

A pharmaceutical composition containing a compound of formula (I), or a pharmaceutically acceptable salt thereof, may be presented in discrete units such as tablets, capsules, ampules or suppositories, each containing an effective amount of the compound or salt for treatment of migraine.

As an example, for the treatment of humans having migraines the preferred unit dosage of a compound of formula (I) as the hydrochloride salt thereof for oral administration is about 10 mg to 450 mg, preferably 50 mg to 300 mg, and the most preferred unit dosage of 100 to 200 mg optionally given in divided doses. Treatment is preferably initiated at the first (prodromal) symptom of a migraine.

The compound of formula (I) may also be administered prophylactically, e.g., at a preferred dose of 100 mg per day, especially for patients suffering frequent migraines.

A compound of formula (I) or pharmaceutically acceptable salts thereof may be presented as an oral unit preparation (for example as a cachet, tablet or capsule) containing one or more pharmaceutically acceptable carriers which may take the form of solid diluents such as lactose, cornstarch, micronized silica gel as well as other excipients known in the art.

It should be understood that in addition to the aforementioned ingredients, the pharmaceutical composition of this invention may include one or more of additional ingredients e.g., pharmaceutically acceptable carriers such as diluents, buffers, flavouring agents, binders, surface active agents, thickeners, lubricants, preservatives, and the like. The formulations may be prepared by admixture of the ingredients, and, if necessary, shaping the resulting mass, and filling into suitable containers.

A preferred pharmaceutical formulation comprises bupropion hydrochloride (100 mg) and caffeine (200 mg) and a pharmaceutically acceptable carrier therefor.

The compound used in this invention is preferably presented for use as a pharmaceutically acceptable acid addition salt. Examples of some of the pharmaceutically acceptable salts which can be utilized are salts of the following acids: hydrochloric, sulfuric, phosphoric and toluenesulphonic.

Reference should be had to U.S. Pat. Nos. 3,819,706 and 3,885,046, which are incorporated herein by reference hereto for a description of the preparation of the compound of formula (I), acid addition salts thereof, tablets, capsules, parenteral solutions and suppositories incorporating same.

I claim:

1. A method of treating migraine in a human suffering from same which comprises administering to said human an effective migraine treating amount of bupropion hydrochloride.

2. A method according to claim 1 wherein an effective amount of caffeine is also administered.

3. A pharmaceutical formulation consisting essentially of an effective migraine treating amount of bupropion hydrochloride and caffeine and a pharmaceutically acceptable carrier therefor.

* * * * *